United States Patent
Godenschwager et al.

(10) Patent No.: US 10,964,120 B2
(45) Date of Patent: Mar. 30, 2021

(54) METHOD FOR THE IDENTIFICATION OF SUPPLY AREAS, METHOD FOR THE GRAPHICAL REPRESENTATION OF SUPPLY AREAS, COMPUTER PROGRAM, MACHINE-READABLE MEDIUM AND IMAGING DEVICE

(71) Applicant: Siemens Aktiengesellschaft, Munich (DE)

(72) Inventors: Christian Godenschwager, Bamberg (DE); Michael Suehling, Erlangen (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 1115 days.

(21) Appl. No.: 14/963,324

(22) Filed: Dec. 9, 2015

(65) Prior Publication Data
US 2016/0180052 A1    Jun. 23, 2016

(30) Foreign Application Priority Data
Dec. 19, 2014    (DE) .......................... 102014226685.8

(51) Int. Cl.
*G06T 19/20*    (2011.01)
*A61B 6/03*    (2006.01)
(Continued)

(52) U.S. Cl.
CPC ............. *G06T 19/20* (2013.01); *A61B 6/032* (2013.01); *A61B 6/481* (2013.01); *A61B 6/503* (2013.01);
(Continued)

(58) Field of Classification Search
CPC ............. G06T 19/20; G06T 2210/41; G06T 2219/2012; G16H 50/50; A61B 6/032;
(Continued)

(56) References Cited

U.S. PATENT DOCUMENTS 8,010,175 B2   8/2011   O'Donnell
8,831,314 B1   9/2014   Fonte
(Continued)

FOREIGN PATENT DOCUMENTS

CN   102551780 A   7/2012
CN   103270513 A   8/2013
(Continued)

OTHER PUBLICATIONS

Yamaguchi et al., Particle-Based Methods for Multiscale Modeling of Blood Flow in the Circulation and in Devices: Challenges and Future Directions, Ann Biomed Eng. Mar. 2010 ; 38(3): 1225-1235.*

(Continued)

*Primary Examiner* — Bo Joseph Peng
(74) *Attorney, Agent, or Firm* — Harness, Dickey & Pierce, P.L.C.

(57) ABSTRACT

An embodiment of the invention is based on the idea of adjusting a physiological model of an anatomical region containing blood vessels on the basis of patient-specific 3D image data of the anatomical region. Since the physiological model includes at least one geometric parameter as well as functional parameters, in particular the at least one geometric parameter and/or the functional parameters can be adjusted. The 3D perfusion of the anatomical region is now simulated on the basis of the adjusted physiological model such that the patient-specific supply areas of the anatomical region are identified on the basis of the simulation.

33 Claims, 5 Drawing Sheets

(51) Int. Cl.
- *A61B 6/00* (2006.01)
- *G06F 19/00* (2018.01)
- *G16H 50/50* (2018.01)

(52) U.S. Cl.
CPC .............. *A61B 6/504* (2013.01); *G06F 19/00* (2013.01); *G16H 50/50* (2018.01); *G06T 2210/41* (2013.01); *G06T 2219/2012* (2013.01)

(58) Field of Classification Search
CPC ......... A61B 6/481; A61B 6/503; A61B 6/504; G06F 19/00
See application file for complete search history.

(56) References Cited

U.S. PATENT DOCUMENTS

| | | |
|---|---|---|
| 9,226,672 B2 † | 1/2016 | Taylor |
| 2012/0041318 A1 | 2/2012 | Taylor |
| 2012/0053918 A1 | 3/2012 | Taylor |
| 2012/0121151 A1 | 5/2012 | Bernhardt et al. |
| 2014/0114618 A1 | 4/2014 | Fonte |
| 2014/0249399 A1 | 9/2014 | Sharma |
| 2014/0294137 A1 | 10/2014 | Bernhardt et al. |
| 2015/0193574 A1 | 7/2015 | Bernhardt et al. |

FOREIGN PATENT DOCUMENTS

| | | |
|---|---|---|
| DE | 102005035181 A1 | 3/2006 |
| DE | 102010043849 B3 | 2/2012 |
| DE | 102012206542 A1 | 10/2013 |
| EP | 2538361 A2 | 12/2012 |
| WO | WO 2006010609 A2 | 2/2006 |
| WO | WO 2006010609 A3 | 10/2006 |
| WO | WO 2014062946 A1 | 4/2014 |

OTHER PUBLICATIONS

Michael H. Buonocore, Visualizing blood flow patterns using streamlines, arrows, and particle paths, MRM 40:210-226, 1998.*

Munoz et. al. (Intracardiac flow visualization: current status and future directions, European Heart Journal—Cardiovascular Imaging, 2013, 14, 1029-1038, online published on Aug. 1, 2013.*

Arzani et al., Lagrangian postprocessing of computational hennodynannics, Ann Biomed Eng. Jan. 2015; 43(1): 41-58, Published online Jul. 25, 2014.*

Beliveau P. et al.: "Computation of Coronary Perfusion Territories from CT Angiography", in: Computers in Cardiology, 2007, vol. 34, pp. 753-756, ISSN 0276-6574.

Cerqueira Manuel D. et al.: "Standardized Myocardial Segmentation and Nomenclature for Tomographic Imaging of the Heart", in: Journal of Cardiovascular Magnetic Resonance, 2002, vol. 4(2), pp. 203-210.

Termeer Maurice et al.: "Patient-Specific Mappings between Myocardial and Coronary Anatomy", in: ACM Subject Classification, 1998, pp. 196-209, DOI: 10.4230/DFU.SciViz.2010.196.

Cerqueira Manuel D. et al.: "Standardized Myocardial Segmentation and Nomenclature for Tomographic Imaging of the Heart", in: Circulation 2002; vol. 105; pp. 539-542; 2002.

Sensky Penelope R. et al.: "Interpreting Regional Myocardial Magnetic Resonance Imaging Data: A New Method for Collation with Angiographic Findings in Patients with Coronary Artery Disease", in: Clinical Radiology, 2002, vol. 57, pp. 498-501, DOI:10.1053/crad.2001.0924.

Termeer Maurice et al.: "Visualization of Myocardial Perfusion Derived from Coronary Anatomy", in: IEEE Transactions on Visualization and Computer Graphics, vol. 14, No. 6, Nov./Dec. 2008, pp. 1595-1602.

German Office Action dated Oct. 9, 2015.

Chinese Office Action and English translation thereof dated Oct. 9, 2017.

Chinese Office Action and partial English translation thereof dated Jun. 4, 2019.

Chinese Office Action and partial English translation thereof dated Feb. 1, 2021.

\* cited by examiner
† cited by third party

METHOD FOR THE IDENTIFICATION OF SUPPLY AREAS, METHOD FOR THE GRAPHICAL REPRESENTATION OF SUPPLY AREAS, COMPUTER PROGRAM, MACHINE-READABLE MEDIUM AND IMAGING DEVICE

PRIORITY STATEMENT

The present application hereby claims priority under 35 U.S.C. § 119 to German patent application number DE 102014226685.8 filed Dec. 19, 2014, the entire contents of which are hereby incorporated herein by reference.

FIELD

At least one embodiment of the invention generally relates to a method for the identification of supply areas, a method for the graphical representation of supply areas, a computer program, a machine-readable medium and/or an imaging device.

BACKGROUND

Anatomical regions, in particular muscular tissue and internal organs, must be supplied with blood in order to enable them to perform their function. Areas of such an anatomical region which are supplied with blood can also be referred to as supply areas. A supply area is typically identified on the basis of the particular blood vessel which supplies the supply area with blood. The identification of supply areas within an anatomical region is very important for diagnosis and treatment planning. This applies in particular when the supply areas of the myocardium are to be identified. Although it is possible to identify damaged areas of the myocardium by way of a perfusion measurement, a correct patient-specific identification is however rendered more difficult by the high anatomical variability of the coronary tree. In addition, the hemodynamic effects of pathological changes to the coronary arteries on the distribution of the supply areas can be estimated only with difficulty.

In the article "Standardized myocardial segmentation and nomenclature for tomographic imaging of the heart. A statement for healthcare professionals from the Cardiac Imaging Committee of the Council on Clinical Cardiology of the American Heart Association", published in Circulation (2002), 105(2), pp. 539 to 542, Cerqueira et al. propose a uniform coordinate system and a uniform subdivision of the myocardium. Furthermore, according to Cerqueira et al., subtrees of the coronary tree are also assigned to the defined segments. Said segmentation of the supply areas of the myocardium is well established and is used as a standard inter alia by the American Heart Association (AHA). Said segmentation is also known as the 17-segment model. The disadvantage of a conventional identification of supply areas by way of the 17-segment model and also other known models is the fact that the wide variability of the coronary tree is not taken into consideration.

SUMMARY

An embodiment of the present invention specifies an improved identification of supply areas.

Embodiment of the present invention are directed to methods, computer programs, machine-readable media, and imaging devices.

An embodiment of the invention is based on the idea of adjusting a physiological model of an anatomical region containing blood vessels on the basis of patient-specific 3D image data of the anatomical region. Since the physiological model comprises at least one geometric parameter as well as functional parameters, in particular the at least one geometric parameter and/or the functional parameters can be adjusted. The 3D perfusion of the anatomical region is now simulated on the basis of the adjusted physiological model such that the supply areas of the anatomical region are identified on the basis of the simulation.

An embodiment of the invention thereby enables identification of the supply areas on a patient-specific basis. The supply areas according to an embodiment of the invention can therefore also be referred to as patient-specific supply areas. This is because the adjustment of the physiological model is carried out on the basis of patient-specific 3D image data. In particular, parameters of the physiological model such as the at least one geometric parameter or the functional parameters can be adjusted to parameters which are derived from the patient-specific 3D image data. Geometric parameters can be derived from patient-specific 3D image data with great precision by way of modern imaging techniques such as tomography. If at least one part of the patient-specific 3D image data has been acquired by way of functional imaging, then functional parameters can also be derived from the patient-specific 3D image data.

Furthermore, an embodiment of the invention relates to a method for the graphical representation of supply areas, wherein a simulation of a 3D perfusion of an anatomical region containing blood vessels takes place on the basis of a physiological model of the anatomical region, in which case the physiological model comprises at least one geometric parameter as well as functional parameters. Furthermore, with the method the supply areas of the anatomical region are identified on the basis of the simulation. Finally, a graphical representation takes place of at least one part of the blood vessels, in which case at least one distribution calculated by the simulation is displayed in color-coded fashion.

Furthermore, an embodiment of the invention relates to computer programs having program code segments for performing the method steps according to an embodiment of the invention when the respective computer program is executed in a computer. Such a computer program can also be executed simultaneously on a plurality of computers, in particular on a so-called "cluster" of computers. In this situation the computer program can be executed by way of distributed computing on a plurality of computers.

Furthermore, an embodiment of the invention relates to machine-readable media on which such a computer program is executed. The computer program and the machine-readable medium can in each case be integrated into an imaging device or a so-called "workstation" in order to process 3D image data. Furthermore, the computer program and the machine-readable medium can also be present spatially separated from an imaging device, in particular the patient-specific 3D image data can be transferred over a network, for example the internet or an intranet, for processing by the computer program. The computer program or the machine-readable medium can thus also be embodied as a client, in which case the patient-specific 3D image data can be stored in retrievable fashion on a server, in particular an image filing and communication system. Such a server can be embodied both centrally and also decentrally, in particular in the form of a so-called "cloud". In order to ensure data security when patient-specific 3D image data or parameters derived therefrom are being transferred, these can be encrypted when being transferred over a network.

BRIEF DESCRIPTION OF THE DRAWINGS

The invention will be described and explained in detail in the following with reference to the example embodiments illustrated in the figures. The supply areas described in the figures can in particular be embodied as patient-specific supply areas.

In the drawings.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Further, although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

An embodiment of the invention is based on the idea of adjusting a physiological model of an anatomical region containing blood vessels on the basis of patient-specific 3D image data of the anatomical region. Since the physiological model comprises at least one geometric parameter as well as functional parameters, in particular the at least one geometric parameter and/or the functional parameters can be adjusted. The 3D perfusion of the anatomical region is now simulated on the basis of the adjusted physiological model such that the supply areas of the anatomical region are identified on the basis of the simulation.

An embodiment of the invention thereby enables identification of the supply areas on a patient-specific basis. The supply areas according to an embodiment of the invention can therefore also be referred to as patient-specific supply areas. This is because the adjustment of the physiological model is carried out on the basis of patient-specific 3D image data. In particular, parameters of the physiological model such as the at least one geometric parameter or the functional parameters can be adjusted to parameters which are derived from the patient-specific 3D image data. Geometric parameters can be derived from patient-specific 3D image data with great precision by way of modern imaging techniques such as tomography. If at least one part of the patient-specific 3D image data has been acquired by way of functional imaging, then functional parameters can also be derived from the patient-specific 3D image data.

Furthermore, the simulation of the 3D perfusion is carried out on the basis of the adjusted physiological model. The results of such a simulation exhibit a considerably higher spatial and temporal resolution than a conventional perfusion measurement. The supply areas can therefore also be determined very precisely using the proposed method.

According to an embodiment of an aspect of the invention, the 3D extent of the blood vessels relative to the anatomical region is adjusted as a first geometric parameter on the basis of the patient-specific 3D image data. In particular, bifurcation points and/or the local bends von blood vessels can be adjusted in this situation. By way of an embodiment of the aspect it is furthermore possible to adjust at least one exit point of a blood vessel into the tissue of the anatomical region. The extent of the blood vessels influences the characteristics of the flow of the blood in the blood vessels and thereby the simulation of the 3D perfusion. The characteristics in question of the flow of the blood are for example the flow speed, in particular the local variation thereof, or turbulences, in particular in the region of bifurcations. Furthermore, the pressure or a change in pressure in question, in particular in the region of a stenosis, is a characteristic of the flow.

The 3D extent of the blood vessels can be adjusted on the basis of conventional methods of image processing. The blood vessels in the patient-specific 3D image data can thus first be segmented and then centerlines of the blood vessels can be determined on the basis of the segmented blood vessels. The extent, the bifurcation points and the local bends of the blood vessels can be adjusted on the basis of centerlines of the blood vessels. Furthermore, a geometric model of the blood vessels and/or of the anatomical region can be derived from the patient-specific 3D image data. Geometric parameters can then be derived and adjusted on the basis of such a geometric model.

According to an embodiment of an aspect of the invention, at least one diameter of one of the blood vessels is adjusted as a second geometric parameter on the basis of the patient-specific 3D image data. The adjustment of the diameter is of particular importance because it greatly influences the characteristics of the blood flow in the blood vessels and thereby the simulation of the 3D perfusion.

According to an embodiment of an aspect of the invention, the physiological model comprises a 3D structure of the anatomical region. The 3D structure can in particular comprise one or more surfaces of the anatomical region. A knowledge of the 3D structure of the anatomical region means that the 3D perfusion in the anatomical region can be simulated particularly precisely.

According to an embodiment of an aspect of the invention, the anatomical region in question is at least a part of the heart of the patient, in which case the 3D surface structure of the heart is adjusted as a third geometric parameter. The surface structure can furthermore comprise the surface structure of the inner lining of heart, also known as endocardium, and/or the surface structure of the heart sac, also known as epicardium.

According to an embodiment of an aspect of the invention, at least one functional parameter is adjusted to a perfusion parameter obtained from a perfusion measurement of the anatomical region. For example, a perfusion parameter in question is the speed of the blood flow, the transport rate of the blood flow, is the blood volume or is the mean transit time. In particular, the perfusion parameters can in each case be embodied locally in that they relate only to a particular region of a blood vessel.

According to an embodiment of an aspect of the invention, the supply areas are identified as 3D supply areas. The supply areas then in each case constitute a voluminous proportion of the anatomical region. This case is particularly relevant because it permits extraordinarily precise diagnosis or treatment planning.

According to an embodiment of an aspect of the invention, the supply areas are identified independently of predetermined segments of the anatomical region. In particular, the supply areas can be identified independently of the segments of the 17-segment model. The supply areas can thereby be determined in a particularly flexible and individual manner.

According to an embodiment of an aspect of the invention, the anatomical region in question is the heart of a patient, and the blood vessels comprise at least RIVA, RCA and RCX, in which case the supply areas are identified depending on the simulated 3D perfusion of the heart by RIVA, RCA and RCX, wherein RIVA, RCA and RCX stand respectively for ramus interventricularis anterior, right coronary artery and ramus circumflexus. A further common abbreviation used for RIVA is the acronym LAD (left anterior descending).

According to an embodiment of an aspect of the invention, the 3D perfusion is simulated on the basis of a Lattice Boltzmann method. The Lattice Boltzmann method employs methods of statistical physics, wherein a greatly simplified particle microdynamics is employed. Particles in the meaning of the present application can in particular be massless. The simulation thus takes place at the level of individual particles. On account of the good parallelization capability, the Lattice Boltzmann method is suitable for the calculation of flows in complex geometries, in particular on computers having modern multicore architectures or on a plurality of computers via distributed computing. It is however also possible that the 3D perfusion is simulated using other methods of numeric flow simulation.

According to an embodiment of an aspect of the invention, a flow field is calculated on the basis of the simulation, wherein the flow field includes the movement of blood both in the blood vessels and also into tissue of the anatomical region. The supply areas can thereby be determined particularly precisely.

According to an embodiment of an aspect of the invention, paths of particles moved through the flow field are calculated. Said paths can be evaluated in order to analyze the flow field and thereby the supply of the anatomical region with blood. In particular, the supply areas can be identified on the basis of the paths.

According to an embodiment of an aspect of the invention, the particles are produced in one of the blood vessels, in which case the particles are assigned to the particular blood vessel from which they penetrate into the tissue of the anatomical region. According to an alternative aspect, the particles can be produced on a grid within the tissue of the anatomical region, in which case the particles are assigned to the particular blood vessel at which the particles arrive by way of a reverse integration. According to these two aspects, the supply areas can be identified on the basis of the assignment of the particles. This means that the large volume of statistical information available in the case of a large number of particles is utilized to provide a precise identification of the supply areas.

According to an embodiment of an aspect of the invention, a graphical representation takes place of at least one part of the blood vessels, wherein at least one distribution based on the simulation is displayed in color-coded fashion. The results of the simulation are thereby output with a high information density. Furthermore, particularly rapid checking of the results of the simulation is possible on the basis of the graphical representation. Furthermore, the graphical representation facilitates the diagnosis and the treatment planning.

According to an embodiment of an aspect of the invention, the distribution comprises the proportions of the blood vessels in the entire 3D perfusion, which means that the colors of the displayed blood vessels are assigned in each case to the relative proportion of the blood vessel in question in the entire 3D perfusion.

According to an embodiment of an aspect of the invention, the distribution comprises an assignment of the particles to one of the supply areas in each case, wherein the colors of the displayed particles are assigned in each case to one of the supply areas.

According to an embodiment of an aspect of the invention, the distribution comprises a speed distribution of the particles, wherein the colors of the displayed particles or of the displayed paths of the particles are assigned in each case to a speed.

Furthermore, an embodiment of the invention relates to a method for the graphical representation of supply areas, wherein a simulation of a 3D perfusion of an anatomical region containing blood vessels takes place on the basis of a physiological model of the anatomical region, in which case the physiological model comprises at least one geometric parameter as well as functional parameters. Furthermore, with the method the supply areas of the anatomical region are identified on the basis of the simulation. Finally, a graphical representation takes place of at least one part of the blood vessels, in which case at least one distribution calculated by the simulation is displayed in color-coded fashion.

Furthermore, an embodiment of the invention relates to computer programs having program code segments for performing the method steps according to an embodiment of the invention when the respective computer program is executed in a computer. Such a computer program can also be executed simultaneously on a plurality of computers, in particular on a so-called "cluster" of computers. In this situation the computer program can be executed by way of distributed computing on a plurality of computers.

Furthermore, an embodiment of the invention relates to machine-readable media on which such a computer program is executed. The computer program and the machine-readable medium can in each case be integrated into an imaging device or a so-called "workstation" in order to process 3D image data. Furthermore, the computer program and the machine-readable medium can also be present spatially separated from an imaging device, in particular the patient-specific 3D image data can be transferred over a network, for example the internet or an intranet, for processing by the computer program. The computer program or the machine-readable medium can thus also be embodied as a client, in which case the patient-specific 3D image data can be stored in retrievable fashion on a server, in particular an image filing and communication system. Such a server can be embodied both centrally and also decentrally, in particular in the form of a so-called "cloud". In order to ensure data security when patient-specific 3D image data or parameters derived therefrom are being transferred, these can be encrypted when being transferred over a network.

An object or a characteristic which is embodied spatially three-dimensionally is also provided with the prefix "3D" in the context of the present application. Spatially three-dimensional image data is thus also referred to as 3D image data, and a spatially three-dimensional perfusion is also referred to as 3D perfusion. Furthermore, both the patient-specific 3D image data and also the 3D perfusion or further spatially three-dimensionally embodied objects or characteristics can have a temporal component.

A physiological model of an anatomical region models a physiological process of the anatomical region. The blood vessels of the anatomical region can be embodied contiguously and form a vascular system. The physiological model can furthermore differentiate different types of blood vessels, for example arteries, arterioles, capillaries, veins and venules. The physiological process in question can in particular be the supply of the anatomical region with blood. The physiological model can be based on physical processes, in particular flow processes. The physiological model is typically implemented as a computer program. The physiological model can comprise a geometric model as well as a functional model, wherein the geometric model describes the geometry of the anatomical region containing blood vessels, and wherein the functional model describes a physiological process. In this situation the geometric model can set up boundary conditions for the functional model. The geometric model comprises one or more geometric parameters, in which case a geometric parameter can set up a boundary condition for the functional model.

The physiological model comprises at least one geometric parameter as well as functional parameters. A geometric parameter relates to a geometric characteristic of the anatomical region, for example the 3D extent of the anatomical region or the diameter of a blood vessel. The diameter can be determined spatially three-dimensionally insofar as a plurality of diameters within a cross-sectional plane, in particular perpendicular to the centerline, of the blood vessel are determined. It is thereby furthermore possible to determine a constriction of the blood vessel spatially three-dimensionally. The functional parameters in question are for example perfusion parameters or a permeability parameter for the anatomical region. In particular, it can be a permeability parameter which specifies the extent to which blood from a blood vessel enters surrounding tissue or the extent to which blood flows within the tissue. The tissue in question can be myocardium. Furthermore, a functional parameter can be based on a measurement or a calculation. For example, the pressure or the drop in pressure of the blood, in particular in the region of a stenosis, can be measured invasively or can also be calculated. The functional parameter can in particular encompass the so-called "fractional flow reserve" or the so-called "instantaneous wave-free ratio".

Furthermore the physiological model can be based on a learning algorithm. In particular, the geometric model and/or the functional model can be based on a learning algorithm. For example, a multiplicity of pairs of geometric and functional parameters can be determined for the learning. The pairs of geometric and functional parameters can be derived from measurements on patients. On the basis of the pairs the learning algorithm can then establish a relationship between one or more geometric parameters and one or more functional parameters. If a geometric parameter is now derived from the patient-specific 3D image data, not only can a corresponding geometric parameter of the physiological model be adjusted, but as a result of the learned relationship a corresponding functional parameter of the physiological model can also be adjusted. For example, the learning algorithm can learn what pressure is prevailing in the region of a stenosis, in which case the stenosis is described by at least one geometric parameter.

The anatomical region in question can be at least a part of an organ and blood vessels associated therewith. The organ in question can for example be the kidneys, the liver, the heart or the brain of a patient. In this situation the physiological model can provide differing domains for the simulation of the 3D perfusion in a blood vessel and in the tissue of the anatomical region. In particular, the functional parameters can be chosen globally in uniform fashion for the entire physiological model or with local differences. The functional parameters can thus differ for example in the blood vessels and in the tissue of the anatomical region.

3D image data is understood to be spatially three-dimensional digital image data which exhibits voxels. 3D image data comprises in particular 3D image data reconstructed from raw data, wherein raw data means the projections acquired directly by an imaging device. For example, 3D image data can be reconstructed from tomographic raw data via the Feldkamp algorithm or an iterative algorithm or an exact algorithm. The acquisition of 3D image data is therefore to be understood as including the acquisition of raw data, from which 3D image data can be reconstructed. The 3D image data can be present in particular in the form of tomographic slices which means that they comprise a multiplicity of spatially two-dimensional image data items which describe a spatially three-dimensional volume.

An imaging device is generally understood as being a device which is designed for the acquisition of 3D image data. A medical imaging device is designed in order to acquire 3D image data of a living object, for example a person, in particular in such a manner that the acquired image data is suitable for diagnostic purposes. One class of medical imaging devices are X-ray devices, comprising C-arm X-ray devices. A further class of medical devices are tomographic devices, comprising computed tomography devices or magnetic resonance tomography devices. The 3D image data in question can accordingly be X-ray image data or tomographic image data.

The patient-specific 3D image data can be acquired in particular with the aid of a contrast agent. Such media as enhance the display of structures and functions of the body in imaging methods are generally used as contrast agents. In the context of the present application, contrast agents are understood to include both conventional contrast agents such as for example iodine or gadolinium and also tracers such as for example 18F, 11C, 15O or 13N.

Geometric parameters can now be derived from the inventively patient-specific 3D image data, for example by using image processing methods. The 3D image data is patient-specific insofar as it is obtained on the basis of only a single patient. Patient-specific geometric parameters and patient-specific functional parameters can thereby be derived from the 3D image data. The geometric parameters can be derived from the patient-specific 3D image data both automatically and also semi-automatically or manually in various embodiments of the invention. Examples of image processing are rendering, segmentation, changing the image appearance such as contrast or resolution, determination of structures and the characteristics thereof in patient-specific 3D image data such as for example a diameter of a blood vessel or of calcifications and stenoses. A local cicatrization of the anatomical region can also be derived from the patient-specific 3D image data. Furthermore, a vascular tree of the blood vessels or the centerlines of the blood vessels can be ascertained from the patient-specific 3D image data. The 3D extent of the blood vessels can also be derived from a vascular tree of the blood vessels and/or centerlines of the blood vessels.

Perfusion is understood as being the supply of an anatomical region with blood. The 3D perfusion is simulated according to the invention on the basis of the adjusted physiological model. The supply of the tissue of the anatomical region with blood in particular is thereby simulated spatially three-dimensionally. If the physiological model comprises a 3D structure of the anatomical region, the 3D perfusion therefore also takes into consideration the 3D structure, for example the 3D surface structure of the anatomical region. In particular, the simulation can take into consideration the diffusion of blood by the 3D structure of the epicardium.

The simulation of the 3D perfusion produces a spatially considerably more precise result than a perfusion measurement. A perfusion measurement can nevertheless be employed in order to determine a functional parameter. A perfusion measurement is typically carried out through the contrast-enhanced acquisition of a temporal series of patient-specific 3D image data. It is however also possible in the case of magnetic resonance tomography to carry out a perfusion measurement without using a contrast agent.

The supply areas can be identified according to the supply by a blood vessel. The supply areas can therefore be assigned in particular to the blood vessel through which they are supplied. If the anatomical region in question is the heart of a patient having at least the blood vessels RIVA, RCA and RCX, then the supply areas can in each case be assigned to one of said blood vessels. If the anatomical region in question is at least one part of the heart of a patient having at least the blood vessels of the left subtree of the coronary vessels, then the supply areas can in each case be assigned to one of said blood vessels. The blood vessels of the left subtree of the coronary vessels comprise the left main artery as well as RIVA and RCX. The left main artery is also known by the acronym LCA (left coronary artery). The supply areas can in each case only be assigned to one blood vessel, in particular the blood vessel which contributes most to supplying the respective area with blood. The supply areas can however also be assigned to more than one blood vessel. If the anatomical area in question is the heart, in particular the number of identified supply areas can in particular be greater than or less than seventeen.

Figure 1:
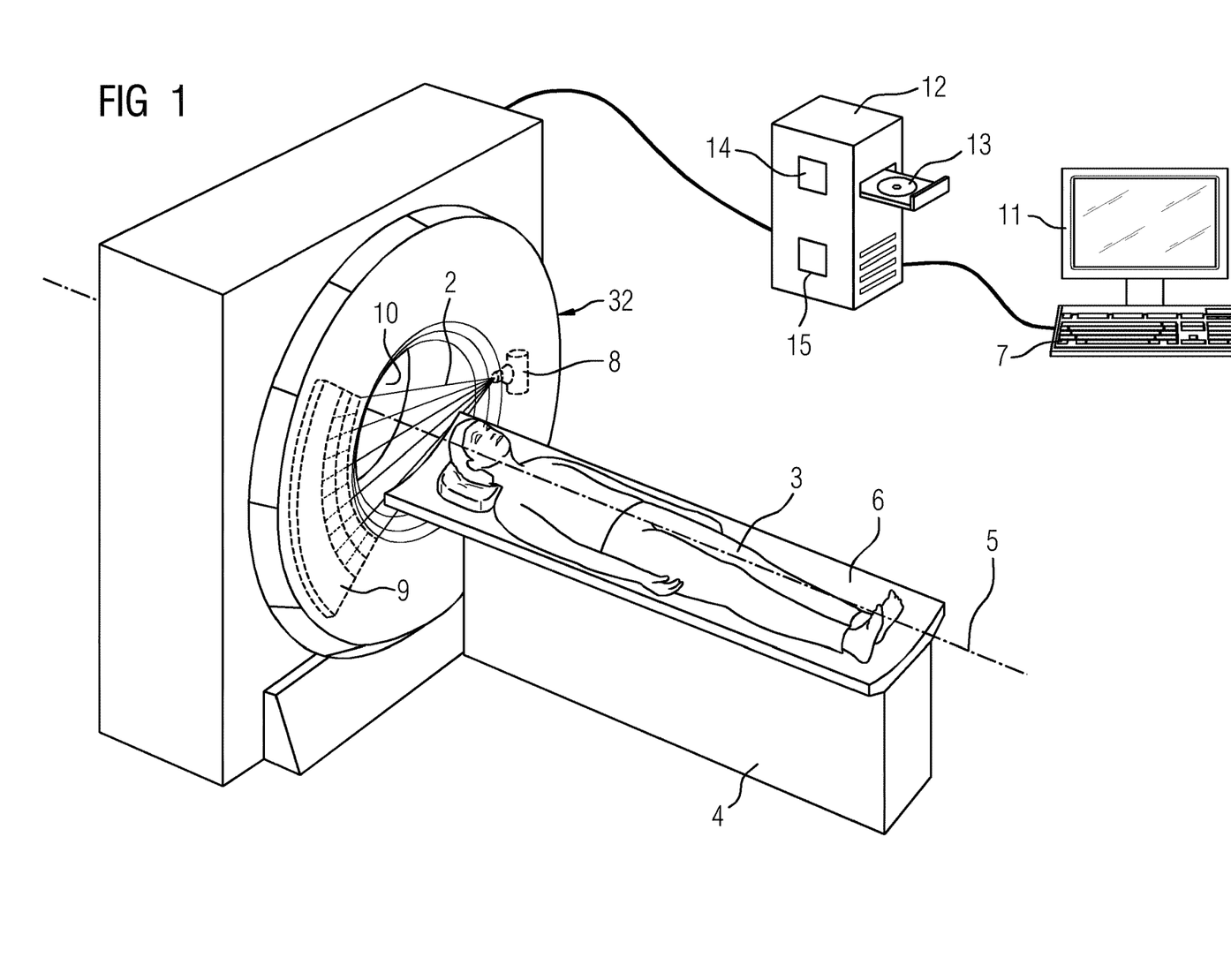
FIG. 1 shows an imaging device having a machine-readable medium according to an embodiment of the invention.

FIG. 1 shows an imaging device having a machine-readable medium according to the invention. Shown here by way of example is a computed tomography device which has an acquisition unit 32 having a radiation source 8 in the form of an X-ray source and also having a radiation detector 9 in the form of an X-ray detector. The acquisition unit 32 rotates about a system axis 5 while X-ray projections are acquired, and the X-ray source emits beams 2 in the form of X-rays during the acquisition. The X-ray source in question in the example shown here is an X-ray tube. The X-ray detector in question in the example shown here is a row detector having a plurality of rows.

In the example shown here, a patient 3 lies on a patient examination table 6 while projections are acquired. The patient examination table 6 is connected to a table pedestal 4 such that it supports the patient examination table 6 carrying the patient 3. The patient examination table 6 is designed in order to transport the patient 3 along a direction of acquisition through the aperture 10 of the acquisition unit 32. The direction of acquisition is given as a general rule by the system axis 5, about which the acquisition unit 32 rotates while X-ray projections are acquired. In the case of a spiral acquisition, the patient examination table 6 is transported continuously through the aperture 10 while the acquisition unit 32 rotates about the patient 3 and acquires X-ray projections. The X-rays thereby describes a spiral on the surface of the patient 3.

In addition, an imaging device can also have a contrast agent injector in order to inject contrast agent into the bloodstream of the patient 3. This means that the images can be acquired by way of a contrast agent in such a manner that structures, in particular blood vessels, lying in the field of examination can be displayed at an increased contrast level. Furthermore, use of the contrast agent injector also offers the possibility of effecting angiographic scans or carrying out a perfusion measurement.

The imaging device shown here has a computer 12 which is connected to a display unit 11 and also to an input unit 7. The display unit 11 in question can for example be an LCD screen, plasma screen or OLED screen. It can furthermore be a touch-sensitive screen which is also embodied as an input unit 7. Such a touch-sensitive screen can be integrated into the imaging device or be embodied as part of a mobile device. The display unit 11 is suitable for the graphical representation PIC according to the invention. The input unit 7 in question is for example a keyboard, a mouse, a so-called "touch screen" or also a microphone for voice input. The input unit 7 is also suitable for selecting a section of the result image output on the display unit 11.

The computer 12 has a reconstruction unit 14 in order to reconstruct patient-specific 3D image data 18 from raw data. For example, the reconstruction unit 14 can reconstruct a tomographic image in the form of an image stack having a plurality of slices. Furthermore, the imaging device can have a computing unit 15. The computing unit 15 can interact with a machine-readable medium 13, in particular in order to carry out a method according to an embodiment of the invention by way of a computer program containing program code.

Furthermore, the computer program can be stored in retrievable fashion on the machine-readable medium 13. In particular, the machine-readable medium in question can be a CD, DVD, Blu-Ray disc, a memory stick or a hard disk. Both the computing unit 15 and also the reconstruction unit 14 can be embodied in the form of hardware or in the form of software. For example, the computing unit 15 or the reconstruction unit 14 is embodied as a so-called FPGA ("field programmable gate array") or comprises an arithmetic logic unit.

In the embodiment shown here at least one computer program, which carries out all the method steps of the method according to an embodiment of the invention when the computer program is executed on the computer 12, is stored in the memory of the computer 12. The computer program for carrying out the method steps of the method according to an embodiment of the invention comprises program code. Furthermore, the computer program can be embodied as an executable file and/or stored on a different computing system to the computer 12. For example, the imaging device can be designed such that the computer 12 loads the computer program for carrying out the method according to an embodiment of the invention into its internal working storage by way of an intranet or via the internet.

Figure 2:
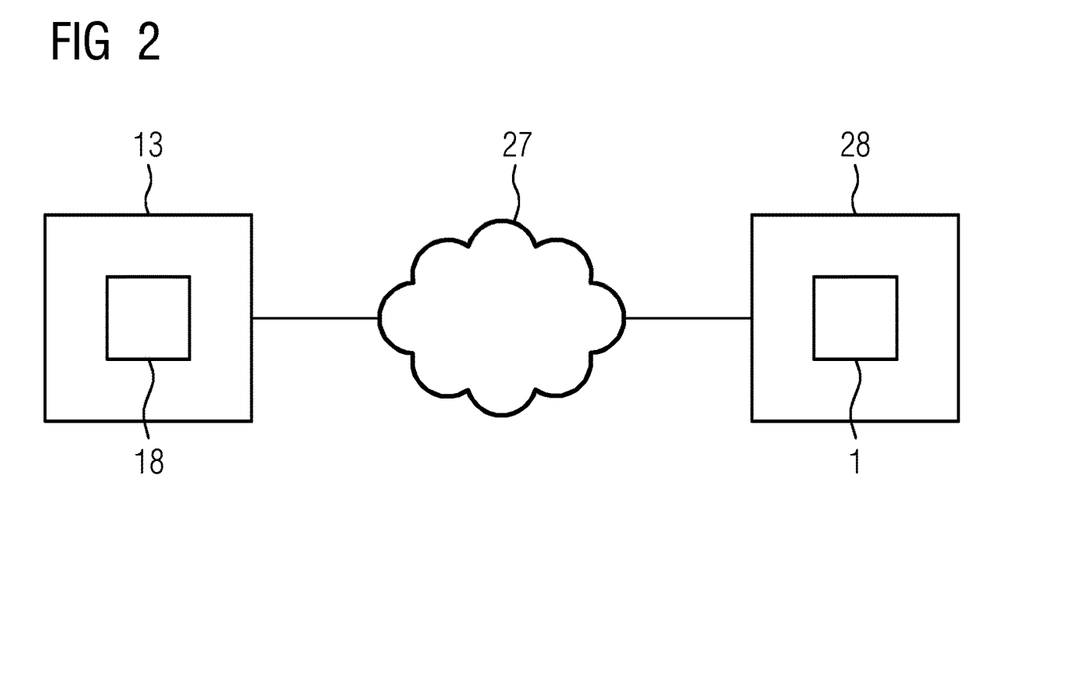
FIG. 2 shows a network having a machine-readable medium.

FIG. 2 shows a network having a machine-readable medium. In the example shown here, the patient-specific 3D image data 18 is stored on the machine-readable medium 13. The patient-specific 3D image data 18 and/or the at least one geometric parameter and/or functional parameters derived therefrom can be transferred to the client 28 over a network 27. The physiological model 1 is stored as an executable program on the client 28. The physiological model 1 can be adjusted by way of the parameters transferred over the network 27 and/or parameters derived from the transferred patient-specific 3D image data 18. A display unit 11 for a graphical representation PIC can be connected directly to the client 28. In further embodiments of the invention, the information relating to the graphical representation PIC is transferred from the client 28 over the network 27 to a display unit 11.

Figure 3:
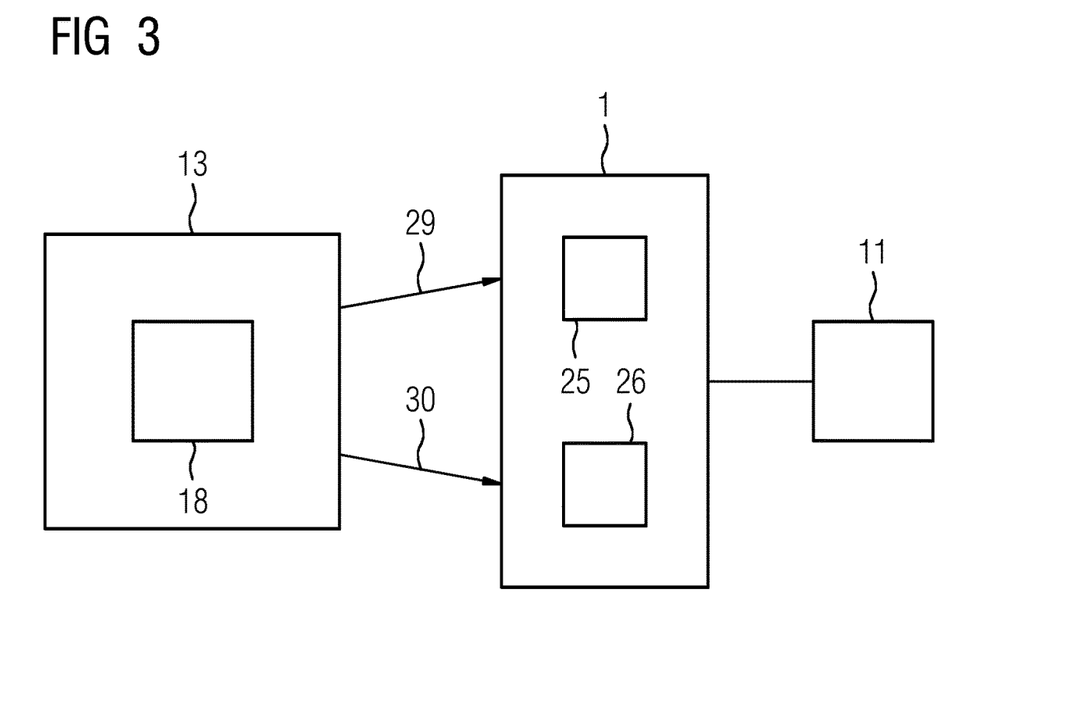
FIG. 3 shows a relationship between different models.

FIG. 3 shows a relationship between different models. In the embodiment shown here of the invention, the physiological model 1 comprises both a geometric model 25 and also a functional model 26. A geometric parameter of the physiological model 1 can be adjusted by a geometric parameter with a first value 29 which has been derived from the patient-specific 3D image data 18. Furthermore, a functional parameter of the physiological model 1 can be adjusted by a functional parameter with a second value 30. Such a functional parameter with the second value 30 can also be derived from the patient-specific 3D image data 18. The 3D image data 18 is stored on a machine-readable medium 13 and furthermore geometric parameter with the first value 29 and the functional parameter with the second value 30 can likewise be stored on the machine-readable medium 13. Furthermore, in a further embodiment of the invention, the geometric parameter with the first value 29 and also the functional parameter with the second value 30 can also be entered manually or selected from a list.

Figure 4:
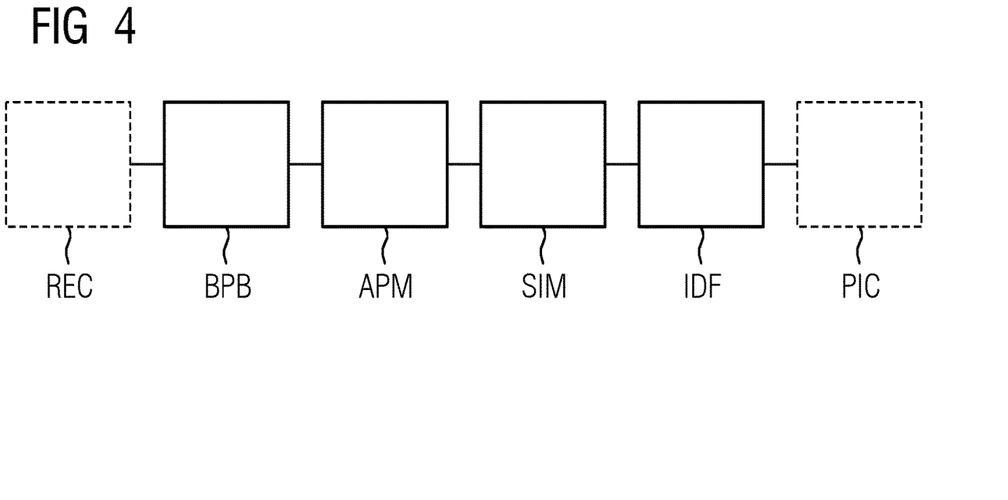
FIG. 4 shows a first flowchart of a method for the identification of supply areas.

FIG. 4 shows a first flowchart of a method for the identification of supply areas. In the embodiment shown here, the method comprises the steps for the determination BPB of a physiological model 1 of an anatomical region 16 containing blood vessels. In this situation the physiological model 1 comprises at least one geometric parameter as well as functional parameters. The determination step BPB can in particular be embodied in such a manner that a retrievably stored physiological model 1 is retrieved into the memory of a computer 12. The determination step BPB can also consist in selecting a particular physiological model 1 from a multiplicity of physiological models 1. For example, differing physiological models 1 can relate to different anatomical regions 16.

Furthermore, the method shown here comprises the step for the adjustment APM of the physiological model 1 on the basis of patient-specific 3D image data 18 of the anatomical region 16. Through the adjustment APM, the physiological model 1 is likewise embodied in patient-specific fashion. The adjusted physiological model 1 thus models a patient-specific physiological process.

The method includes the simulation SIM of the 3D perfusion of the anatomical region 16 on the basis of the adjusted physiological model 1. The physiological process is thereby simulated in patient-specific fashion. For example, this is a numeric simulation, which furthermore can be embodied as a flow simulation. For the purpose of the simulation, in addition to a Lattice Boltzmann method, a so-called CFD simulation can also be carried out (CFD is the acronym for the expression "computational fluid dynamics"). The simulation can take place not only on a local computer 12 but can also be carried out simultaneously via distributed computing on a multiplicity of computers 12.

The method includes the step for the identification IDF of supply areas of the anatomical region 16 on the basis of the simulation. The supply areas can be identified depending on or independently of a predetermined segmentation of the anatomical region. An identification independent of a predetermined segmentation has the advantage that it is particularly flexible and permits a very precise assignment of the supply areas to the respective blood vessels supplying them. Furthermore, the number of supply areas can be specified at the start of the simulation; it can for example correspond to a particular number of blood vessels.

If on the other hand the identification takes place depending on a predetermined segmentation, this has the advantage of a greater standardization. For example, the blood volume which penetrates from a particular blood vessel into a particular segment or is situated at a particular point in time in the simulation in the particular segment, can be recorded. In particular, the blood volume can be represented by particles 24 transported by a simulated flow field. The particular segment is then assigned to the particular blood vessel from which the greatest proportion of the blood volume situated in the particular segment originates. The invention therefore also makes it possible to use a conventional segmentation as the basis for the identification IDF of patient-specific supply areas, in particular of patient-specific 3D supply areas.

In further embodiments of the invention, the method for the identification of supply areas also comprises the acquisition REC of patient-specific 3D image data 18, in particular by way of a tomographic device. A further optional step is the graphical representation PIC of at least one part of the blood vessels, in which case at least one distribution based on the simulation is displayed in color-coded fashion.

Furthermore, the supply of the supply areas can also be determined on the basis of the simulation. This is because the anatomical region 16 may be damaged in the event of an inadequate supply. Furthermore, the determination of the supply can take place in such a manner that an adequate or inadequate supply is indicated, in particular in the form of a graphical representation PIC. In an embodiment, if the supply of a supply area is inadequate, a treatment proposal can also be made automatically for the anatomical region.

Figure 5:
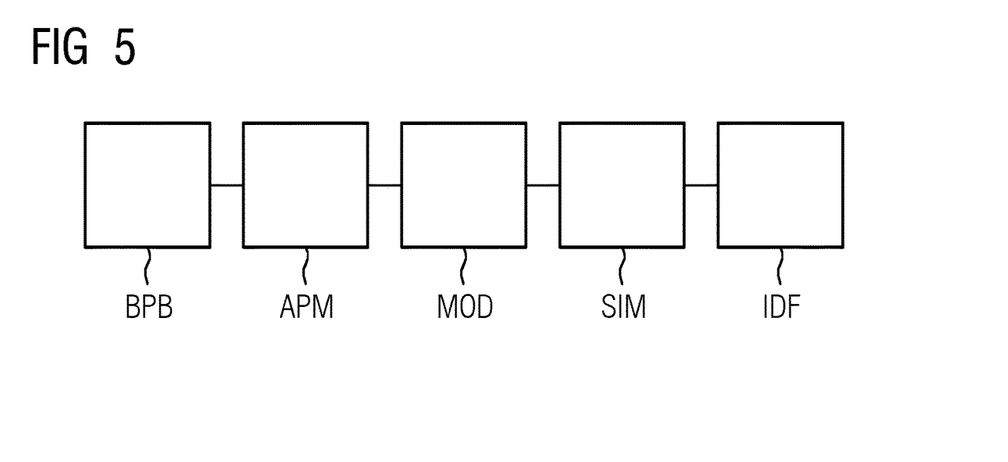
FIG. 5 shows a second flowchart of a method for the identification of supply areas.

FIG. 5 shows a second flowchart of a method for the identification of supply areas. The example shown here includes the step for modification MOD of the physiological model 1. The modification MOD of the physiological model 1 comprises the modification MOD of a geometric or functional parameter. The modification MOD thus also comprises the modification MOD of a geometric model 25 or a functional model 26. The modification MOD takes place in such a manner that the effect of a treatment of the patient 3 is taken into consideration. For example, the modification MOD can take place in such a manner that it corresponds to expanding the lumen of a blood vessel, in particular by way of a stent. The modification MOD can also take place in such a manner that it corresponds to the addition of a bypass. The modification MOD can take place both manually and also semi-automatically. A geometric model 25 can be modified manually through user interaction, for example by using a mouse or another input unit 7. A geometric model 25 can also be modified semi-automatically in that a treatment option is proposed and said treatment option is selected manually through user interaction. Furthermore, the proposal for a particular treatment option can be based on a prior simulation according to an embodiment of the invention.

Figure 6:
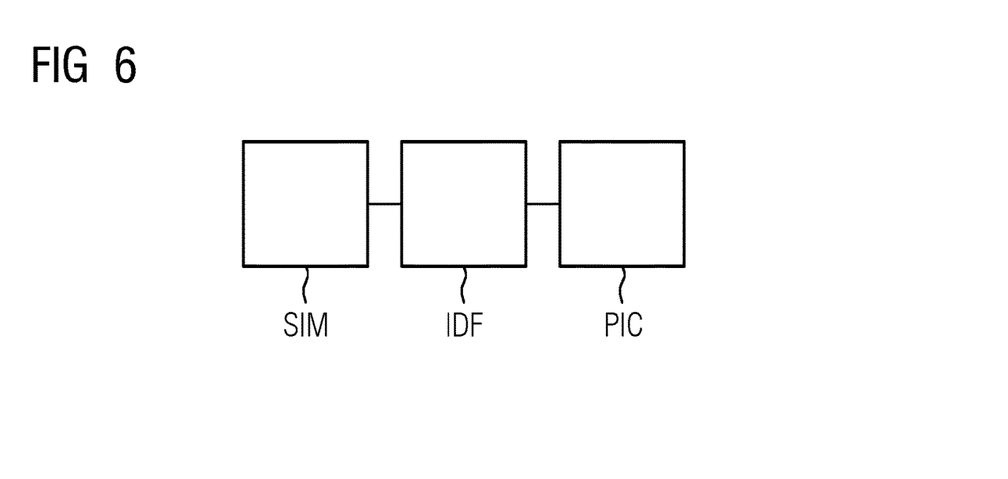
FIG. 6 shows a flowchart of a method for the graphical representation of supply areas.

FIG. 6 shows a flowchart of a method for the graphical representation of supply areas. In this situation the distribution is displayed in color-coded fashion insofar as a particular color property is assigned to a particular value or value range of a distribution. For example, the particles 24 which are assigned to the same blood vessel can in each case be displayed by the same color. Different color scales can be employed in this situation. The color coding can relate both to the color property of the color shade and also to other color properties, for example the saturation. Further embodiments of the method for the graphical representation of supply areas can also comprise the steps of the method for the identification of supply areas, in particular the steps shown in FIG. 4 and FIG. 5.

Figure 7:
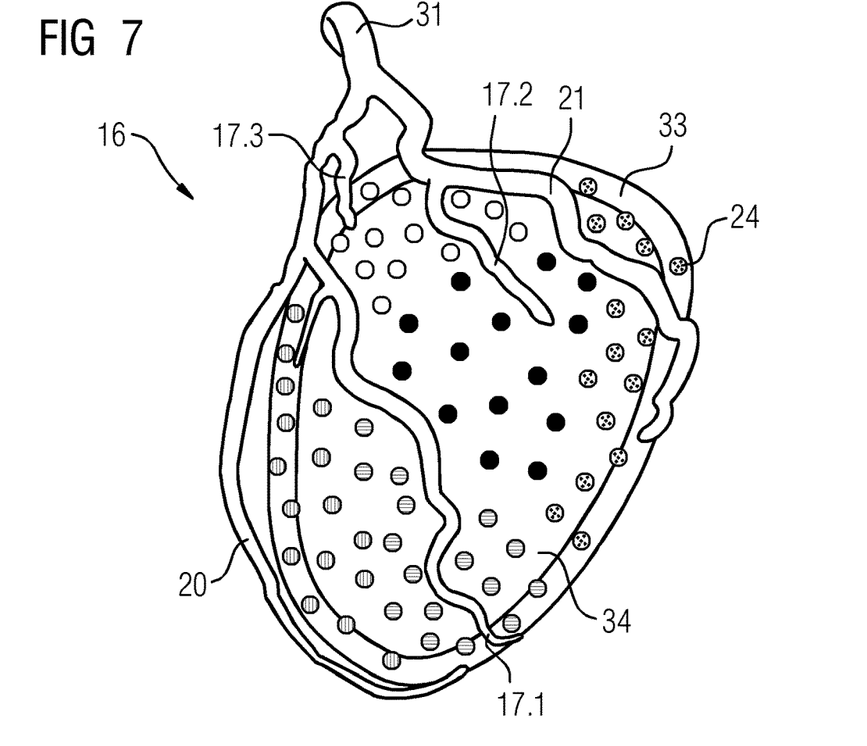
FIG. 7 shows a first graphical representation of a simulation result.

FIG. 7 shows a first graphical representation of a simulation result. In the example shown here, the anatomical region 16 in question is the heart of a patient. In this case the left ventricle 34 with the heart wall 33 is illustrated. In the view shown here, the left subtree of the coronary vessels with the left main artery 31 and also the RIVA 20 and RCX 21 and also three further blood vessels 17.1, 17.2 and 17.3 are illustrated. In this situation, the following assignment applies between the particles 24 having the following filling and the blood vessels: horizontal hatching=first blood vessel 17.1; solid=second blood vessel 17.2; blank=third blood vessel 17.3; vertical hatching=RIVA 20; dotted=RCX 21. The blank filling can thus correspond to the color shade yellow in a color display; the horizontal hatching filling can correspond to the color shade blue in a color display; the vertical hatching filling can correspond to the color shade violet in a color display; the solid filling can correspond to the color shade red in a color display; the dotted filling can correspond to the color shade green in a color display. Other color shades and/or color combinations can be used in further embodiments of the invention.

Figure 8:
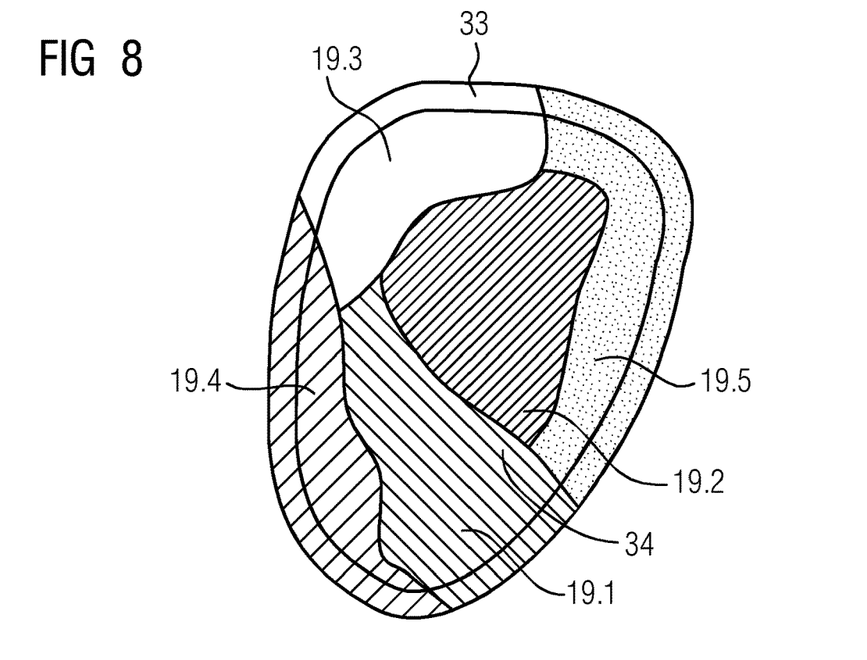
FIG. 8 shows a simplified graphical representation of the patient-specific supply areas.

The particles 24 can also be represented by symbols others than the circles used here. It is thereby possible to identify supply areas in a simple manner. A simplified graphical representation PIC of the supply areas is shown in FIG. 8. The first, second and third supply areas 19.1, 19.2, 19.3 are assigned in FIG. 8 to the three blood vessels 17.1, 17.2 and 17.3. The fourth supply area 19.4 is assigned to RIVA 20. The fifth supply area 19.5 is assigned to RCX 21. In order to increase clarity the blood vessels are not illustrated in FIG. 8. In further embodiments of the invention, the blood vessels can however be displayed together with the identified supply areas. The supply areas can be represented both in a 3D display of the anatomical region 16 and also schematically, in particular spatially two-dimensionally. Furthermore, the identified supply areas can be displayed in color-coded fashion.

In addition, the proportion of the individual blood vessels in the entire regional perfusion can be represented for each position in the myocardium. If for example the graphical representation PIC is restricted to the three main vessels RIVA 20, RCA 21 and LCX 22, then the color coding for the color value F can take place as follows: $F=\alpha R+\beta G+\gamma B$, wherein $\alpha$, $\beta$, $\gamma$ are the relative perfusion proportions of the three main vessels RIVA 20, RCA 21 and LCX 22, and wherein R, G and B are the three primary colors red, green and blue in the RGB color model. Supply area boundaries can be calculated and represented in particular via a watershed transformation.

Figure 9:
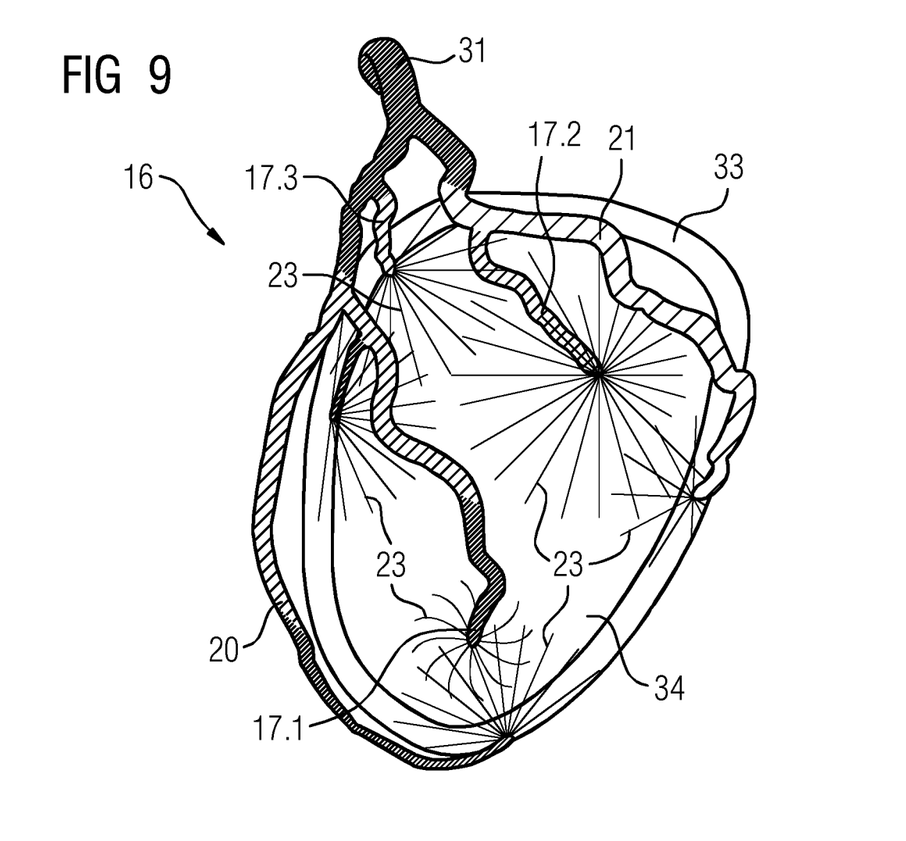
FIG. 9 shows a second graphical representation of a simulation result.

FIG. 9 shows a second graphical representation of a simulation result. As in FIG. 7, the anatomical region 16 in question here is the heart of a patient. In this case the left ventricle 34 with the heart wall 33 is illustrated. Furthermore, the paths 23 of the particles 24 after exiting from the respective blood vessels are illustrated. Said paths 23 can be calculated on the basis of the simulation. In the example shown here, the speed of the particles 24 in the blood vessels is displayed in color-coded fashion. In a further embodiment of the invention, the paths 23 of the particles 24 can also be displayed in color-coded fashion in accordance with the speed of the particles 24 in the tissue of the anatomical region 16, in particular in the myocardium. In the simplified graphical representation PIC shown here, a dense hatching corresponds to a high speed. Three speed classes are represented in this situation:

slow speed: light hatching;
medium speed: medium hatching;
high speed: dense hatching.

The slow speed may correspond to the color shade blue in a color display; a medium speed may correspond to the color shade green in a color display; and a high speed may correspond to the color shade red in a color display. In further embodiments of the invention other color shades and/or color combinations can also be used.

The aforementioned description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods. Further, elements and/or features of different example embodiments may be combined with each other and/or substituted for each other within the scope of this disclosure and appended claims.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Further, at least one embodiment of the invention relates to a non-transitory computer-readable storage medium comprising electronically readable control information stored thereon, configured in such that when the storage medium is used in a controller of a magnetic resonance device, at least one embodiment of the method is carried out.

Even further, any of the aforementioned methods may be embodied in the form of a program. The program may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for identifying supply areas, comprising:
    determining a physiological model of an anatomical region containing blood vessels, the physiological model including at least one geometric parameter and functional parameters;
    adjusting the physiological model on the basis of patient-specific 3D image data of the anatomical region;
    simulating a 3D perfusion of the anatomical region on the basis of the adjusted physiological model;
    determining a flow field based on the simulating, the flow field indicating movement of blood in the blood vessels and into at least a part of a myocardium of the anatomical region;
    determining paths of particles moved through the flow field; and
    identifying supply areas of the anatomical region on the basis of the simulation, the identifying including graphically representing the paths of the particles after exiting from the blood vessels and penetrating into the at least the part of the myocardium of the anatomical region at at least one exit point of the blood vessels.

2. The method of claim 1, wherein the adjusting adjusts a 3D extent of the blood vessels relative to the anatomical region as a first geometric parameter on the basis of the patient-specific 3D image data.

3. The method of claim 2, wherein the adjusting adjusts at least one diameter of one of the blood vessels as a second geometric parameter on the basis of the patient-specific 3D image data.

4. The method of claim 3, wherein the physiological model comprises a 3D structure of the anatomical region.

5. The method of claim 4, wherein the anatomical region is at least a part of a heart of the patient, and wherein the adjusting adjusts a 3D surface structure of the heart as a third geometric parameter.

6. The method of claim 1, wherein the physiological model comprises a 3D structure of the anatomical region.

7. The method of claim 6, wherein the anatomical region is at least a part of a heart of the patient, and the adjusting adjusts a 3D surface structure of the heart as a first geometric parameter.

8. The method of claim 1, wherein the adjusting adjusts at least one functional parameter as a perfusion parameter based on a perfusion measurement of the anatomical region.

9. The method of claim 1, wherein the identifying identifies the supply areas as 3D supply areas.

10. The method of claim 1, wherein the identifying identifies the supply areas independently of predetermined segments of the anatomical region.

11. The method of claim 1, wherein the anatomical region is a heart of a patient, and the blood vessels comprise at least ramus interventricularis anterior (RIVA), right coronary artery (RCA) and ramus circumflexus (RCX), and wherein the supply areas are identified depending on the simulated 3D perfusion of the heart by the RIVA, the RCA and the RCX.

12. The method of claim 1, wherein the simulating simulates the 3D perfusion on the basis of a Lattice Boltzmann method.

13. The method of claim 1, wherein colored particles of the particles are graphically represented in one of the blood vessels, the colored particles being respectively assigned to the blood vessel from which they penetrate into the at least the part of the myocardium of the anatomical region.

14. The method of claim 13, further comprising:
    graphically representing at least one part of the blood vessels, wherein at least one distribution based on the simulation is displayed in color, wherein the distribution comprises an assignment of the particles to one of the respective supply areas, and wherein colors of the represented particles are respectively assigned to one of the supply areas.

15. The method of claim 1, wherein colored particles of the particles are produced on a grid within the at least the part of the myocardium of the anatomical region, and wherein the colored particles are assigned to the blood vessels at which the particles arrive by way of a reverse integration.

16. The method of claim 15, further comprising:
graphically representing at least one part of the blood vessels, wherein at least one distribution based on the simulation is displayed in color, wherein the distribution comprises an assignment of the particles to one of the respective supply areas, and wherein colors of the represented particles are respectively assigned to one of the supply areas.

17. The method of claim 1, further comprising:
graphically representing of at least one part of the blood vessels, wherein at least one distribution based on the simulation is graphically represented in color.

18. The method of claim 17, wherein the distribution comprises proportions of the blood vessels in the 3D perfusion, colors of the graphically represented part of the blood vessels being respectively assigned to the proportions of the blood vessels in the 3D perfusion.

19. The method of claim 1, further comprising:
graphically representing of at least one part of the blood vessels, wherein at least one distribution based on the simulation is displayed in color, wherein the distribution comprises an assignment of the particles to one of the respective supply areas, and wherein colors of the represented particles are respectively assigned to one of the supply areas.

20. The method of claim 1, further comprising:
graphically representing at least one part of the blood vessels, wherein at least one distribution based on the simulation is graphically represented in color, wherein the distribution comprises a speed distribution of colored particles of the particles and wherein colors of the graphically represented colored particles or of the graphically represented paths of the particles are respectively assigned to a speed.

21. A non-transitory computer readable medium including program code segments for performing the method of claim 1 when the program code segments are executed in a computer.

22. A non-transitory memory, configured to store program code segments for performing the method of claim 1 when the program code segments are executed by a processor of a computer.

23. A method for graphically representing supply areas, comprising:
simulating a 3D perfusion of an anatomical region containing blood vessels on the basis of a physiological model of the anatomical region, wherein the physiological model comprises at least one geometric parameter and functional parameters;
determining a flow field based on the simulating, the flow field indicating movement of blood in the blood vessels and into at least a part of a myocardium of the anatomical region;
determining paths of particles moved through the flow field;
identifying supply areas of the anatomical region on the basis of the simulation; and
graphically representing the paths of the particles after exiting from the blood vessels and penetrating into the at least the part of the myocardium of the anatomical region at at least one exit point of the blood vessels, wherein at least one distribution calculated by the simulation is displayed in color-coded fashion.

24. The method of claim 23, wherein the anatomical region is a heart of a patient, and the blood vessels comprise at least ramus interventricularis anterior (RIVA), right coronary artery (RCA) and ramus circumflexus (RCX), and wherein the supply areas are identified depending on the simulated 3D perfusion of the heart by RIVA, RCA and RCX.

25. The method of claim 24, wherein the distribution comprises proportions of the blood vessels in the 3D perfusion, colors of the graphically represented at least one part of the blood vessels being respectively assigned to the proportions of the blood vessels in the 3D perfusion.

26. The method of claim 23, wherein the distribution comprises proportions of the blood vessels in the 3D perfusion, colors of the graphically represented at least one part of the blood vessels being respectively assigned to the proportions of the blood vessels in the 3D perfusion.

27. The method of claim 23, wherein the particles are produced on a grid within the at least the part of the myocardium of the anatomical region, and wherein the particles are assigned to a particular blood vessel at which the particles arrive by way of a reverse integration.

28. The method of claim 23, wherein the distribution comprises an assignment of the particles to one of the respective supply areas, and wherein colors of the represented particles are respectively assigned to one of the supply areas.

29. The method of claim 23, wherein the distribution comprises a speed distribution of colored particles of the particles, and wherein colors of the graphically represented colored particles or of the graphically represented paths of the particles are respectively assigned to a speed.

30. A non-transitory computer readable medium including program code segments for performing the method of claim 23 when the program code segments are executed in a computer.

31. A non-transitory memory, configured to store program code segments for performing the method of claim 23 when the program code segments are executed by a processor of a computer.

32. An imaging device for the acquisition of patient-specific 3D image data, comprising the processor and the memory of claim 22.

33. An imaging device for the acquisition of patient-specific 3D image data, comprising the processor and the memory of claim 31.

* * * * *